United States Patent
Yu et al.

(10) Patent No.: US 6,445,042 B1
(45) Date of Patent: Sep. 3, 2002

(54) METHOD AND APPARATUS FOR MAKING MOSFETS WITH ELEVATED SOURCE/ DRAIN EXTENSIONS

(75) Inventors: Bin Yu, Sunnyvale; Judy Xilin An, San Jose, both of CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

(21) Appl. No.: 09/687,992

(22) Filed: Oct. 13, 2000

Related U.S. Application Data

(62) Division of application No. 09/334,115, filed on Jun. 15, 1999, now Pat. No. 6,187,642.

(51) Int. Cl.$^7$ .................. H01L 29/76; H01L 29/94; H01L 31/062; H01L 31/113
(52) U.S. Cl. ............... 257/369; 257/371; 257/372; 257/382; 257/900
(58) Field of Search .................. 257/369, 370, 257/371, 372, 382, 900

(56) References Cited

U.S. PATENT DOCUMENTS

| | | | | |
|---|---|---|---|---|
| 5,200,352 A | * | 4/1993 | Pfiester | 437/44 |
| 5,319,232 A | * | 6/1994 | Pfiester | 257/344 |
| 5,496,750 A | * | 3/1996 | Moleshi | 437/41 |
| 5,504,031 A | * | 4/1996 | Hsu et al. | 437/57 |
| 5,539,229 A | * | 7/1996 | Noble, Jr. et al. | 257/301 |
| 5,600,165 A | * | 2/1997 | Tsukamoto et al. | 257/323 |
| 5,693,974 A | * | 12/1997 | Hus et al. | 257/369 |

OTHER PUBLICATIONS

Wong S.S., D.R. Bradbury, D.C. Chen& K.Y. Chiu: "Elevated Source/Drain MOSFET"; IDEM 1984, pp. 634–663.

Mark Rodder and D. Yeakley: "Raised Source/Drain MOSFET with Dual Sidewall Spaces": IEEE Electron Device Letters, vol. 12, Mar. 1991, pp. 89–91.

C.–P. Chao, K.E. Violette, S. Unnikrishnan, M. Nandakumar, R.L., Wise, J.A. Kittl, Q.–Z. Hong, and I.–C. Chen: "Low Resistance Ti or Co Salicided Raised Source/Drain Transistors for Sub–0.13$\mu$m CMOS Technologies": IEDM Technology Digest, Dec. 1997.

* cited by examiner

Primary Examiner—Jerome Jackson, Jr.
Assistant Examiner—Shrinivas H Rao
(74) Attorney, Agent, or Firm—LaRiviere, Grubman & Payne, LLP

(57) ABSTRACT

An improved semiconductor device, such as a MOSFET with raised source/drain extensions on a substrate with isolation trenches etched into the surface of the substrate. The device has thin first dielectric spacers on the side of a gate and gate oxide and extend from the top of the gate to the surface of the substrate. Raised source/drain extensions are placed on the surface of a substrate, which extend from the first dielectric spacers to the isolation trenches. Thicker second dielectric spacers are placed adjacent to the first dielectric spacers and extend from the top of the first dielectric spacers to the raised source/drain extensions. Raised source/drain regions are placed on the raised source/drain extensions, and extend from the isolation trenches to the second dielectric spacers. The semiconductor device has very shallow source drain extensions which result in a reduced short channel effect.

7 Claims, 5 Drawing Sheets

US 6,445,042 B1

METHOD AND APPARATUS FOR MAKING MOSFETS WITH ELEVATED SOURCE/DRAIN EXTENSIONS

RELATED APPLICATION

This application is a divisional patent application of U.S. patent application Ser. No. 09/334,119, entitled METHOD AND APPARATUS FOR MAKING MOSFETS WITH ELEVATED SOURCE/DRAIN EXTENSIONS, filed Jun. 15, 1999 now U.S. Pat. No. 6,187,642 by the same applicants.

FIELD OF THE INVENTION

The present invention relates to MOSFET devices, Even more particularly, the present invention relates to MOSFET devices with raised (or elevated) source/drain extensions

BACKGROUND OF THE INVENTION

In the prior art, MOSFETS wit raised source/drain regions use source/drain extensions to connect a channel with the raised source/drain regions. FIG. 1 is a schematic view of a prior art MOSFET 10 with raised source/drain regions 11. The raised source/drain regions 11 are built on top of a substrate 12 surface. A gate oxide 14 is placed on the surface of the substrate 12 between the raised source/drain regions 11. A gate 15 is placed over the gate oxide 14. Side spacers 16 are placed adjacent to the gate 15 and gate oxide 14 and on the substrate 12, separating the gate 15 and gate oxide 14 from the source/drain regions 11. Source/drain extensions 17 are formed at and below the surface of the substrate 12 extending under the source/drain regions 11, the side spacers 16, and partly under the gate oxide 14 and the gate 15. Isolation trenches 19 are cut into the surface of the substrate 12 around the source/drain extensions 17 to isolate the MOSFET 10. The source/drain extensions 17 may be created through various processes with various doping concentrations. Throughout the specification and claims the phrase "source/drain extensions" will also include source/drain extension type structures created through various means such as lightly-doped-drain (LDD) implants.

Deep source/drain junctions increase short-channel effects. An increased short-channel effect causes an increased off stage leakage current. Elevated or raised source/drain MOS transistors have been developed to achieve shallow junctions while maintaining low sheet resistivity in the source/drain regions, as well as low silicided contact resistance without significantly increasing the junction leakage. Such raised source/drains are discussed in "Elevated Source/Drain MOSFET," by S. S. Wong, et al. in IEDM Tech. Digest, December 1984, p. 634, and in "Raised Source/Drain MOSFET With Dual Sidewall Spacers," by Mark Rodder and D. Yeakley, IEEE Electron Device Letters, Vol, 12(3), March 1991, p. 89, and in "Low Resistance Ti or Co Salicided Raised Source/Drain Transistors For Sub-0.13 µm CMOS Technologies," by C. P. Chao, et al., IEDM Tech. Digest., December 1997. Source/drain junctions have been elevated, however, only in the heavily doped regions. In other words, the junction depths of source/drain extensions have not been reduced in the related art.

BRIEF SUMMARY OF THE INVENTION

Accordingly, the present invention comprises a MOSFET having partially raised source/drain extensions. Advantages of the present invention are reducing short channel effects, providing a MOSFET with shallower source/drain extensions, and providing raised source/drain extensions. Other features of the present invention are disclosed or apparent in the section entitled: "DETAILED DESCRIPTION OF THE INVENTION."

BRIEF DESCRIPTION OF THE DRAWING

For a fuller understanding of the present invention, reference is below made to the accompanying drawing. Reference numbers refer to the same or equivalent parts of the present invention throughout the several figures of the drawing.

DETAILED DESCRIPTION OF THE INVENTION AND BEST MODE OF THE INVENTION

Figure 1:
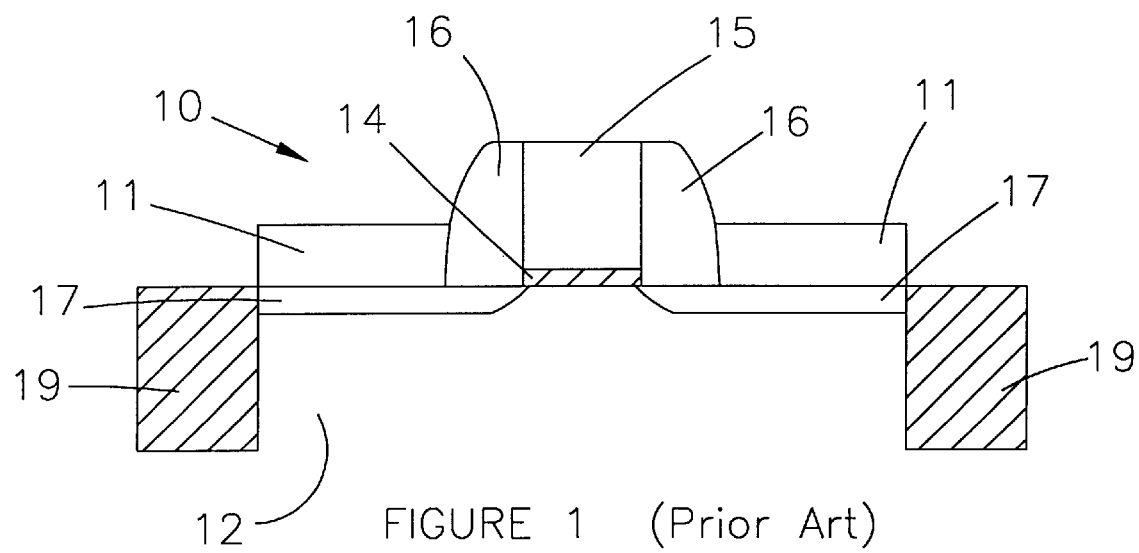
FIG. 1 is a schematic view of a MOSFET used in the prior art.
Figure 2:
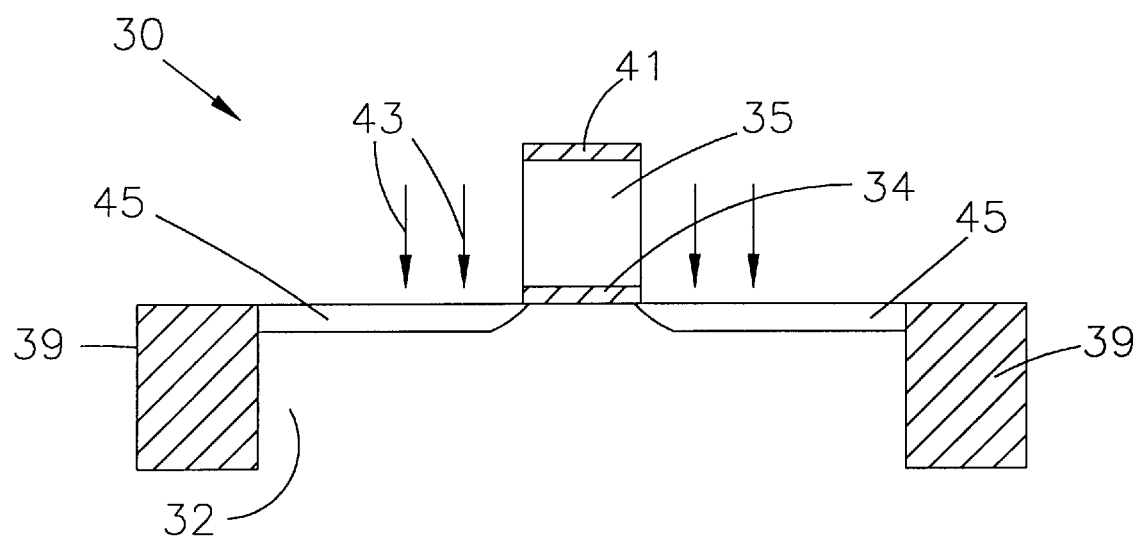
FIG. 2 is a schematic view of a substrate with the first phase of a MOSFET being formed, in accordance with a first embodiment of the present invention.

FIG. 2 is a schematic view of part of a substrate 32 and the first phase of a MOSFET being formed on the substrate 32. Isolation trenches 39 are etched into the surface of the substrate 32. The first phase of the MOSFET 30 has a gate 35 placed on a gate oxide 34 placed on the surface of the substrate 32. An anti-reflective coating (ARC) 41 is placed on the gate 35. In the preferred embodiment, the anti-reflective coating is silicon oxynitride (SiON) with a thickness of 200-300 Å (angstroms). A low-energy (e.g., 1–10 KeV) dopant implantation 43 is used to create very shallow implant junctions 45. In this example of a preferred embodiment, an N-type implant is used.

Figure 3:
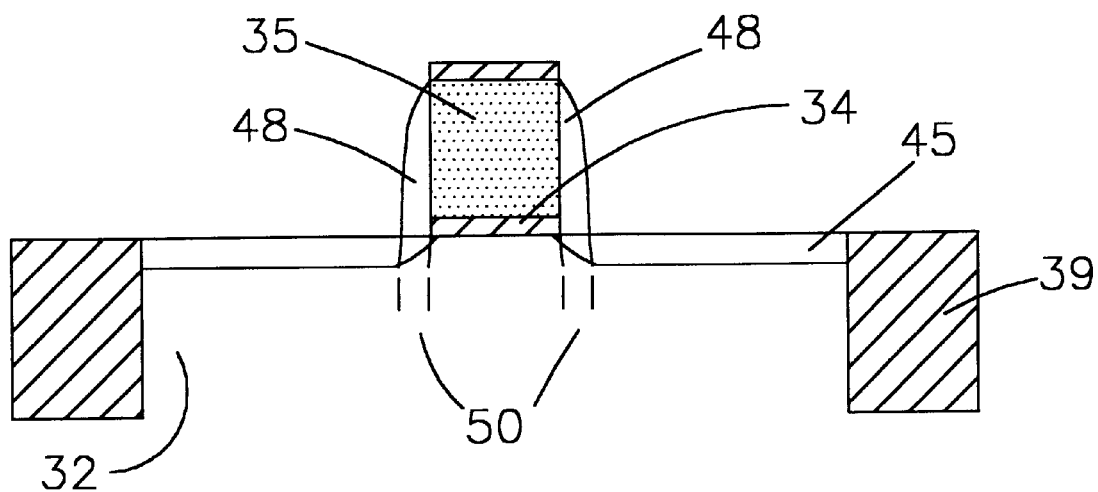
FIG. 3 is a schematic view of the MOSFET in FIG. 2 with first dielectric spacers, in accordance with the first embodiment of the present invention.

In this example of the preferred embodiment, a deposit-and-etch-back process using a low temperature chemical vapor deposition at less than 400° C. is used to form first dielectric spacers 48, which are preferably silicon oxide or silicon nitride, as shown in FIG. 3. The fist dielectric spacers 48 each have a width 50 of between 150–250 Å (which is defined as the thickest part of the width of the first dielectric spacers 48). The first dielectric spacers 48 are adjacent to the sides of the gate 35 and gate oxide 34 and extend from the top of the gate 35 to the surface of the substrate 32.

Figure 4:
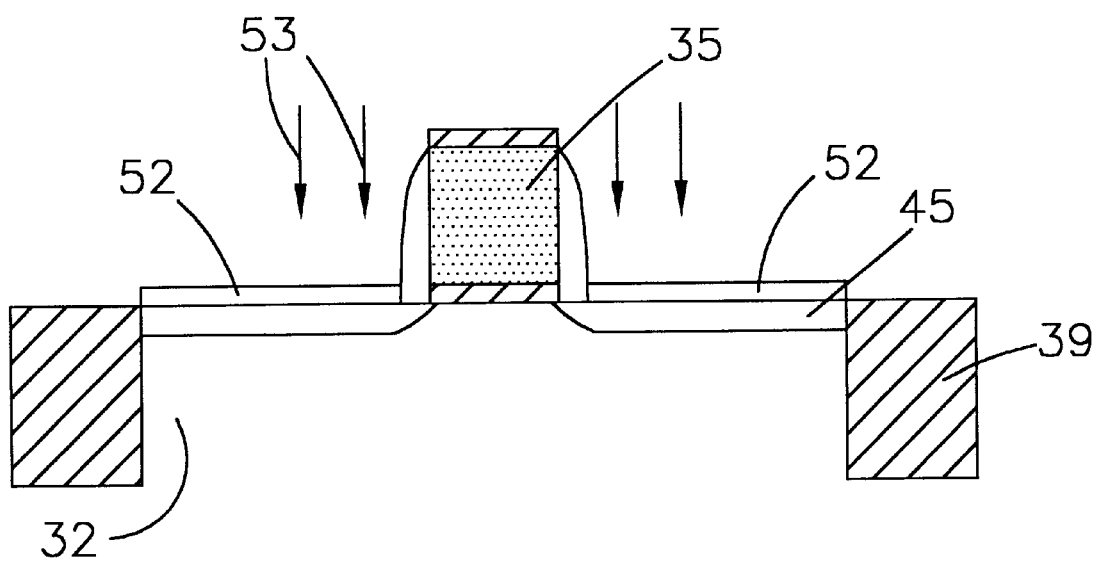
FIG. 4 is a schematic view of the MOSFET in FIG. 3 with a first semiconductor layer, in accordance with the first embodiment of the present invention.
Figure 5:
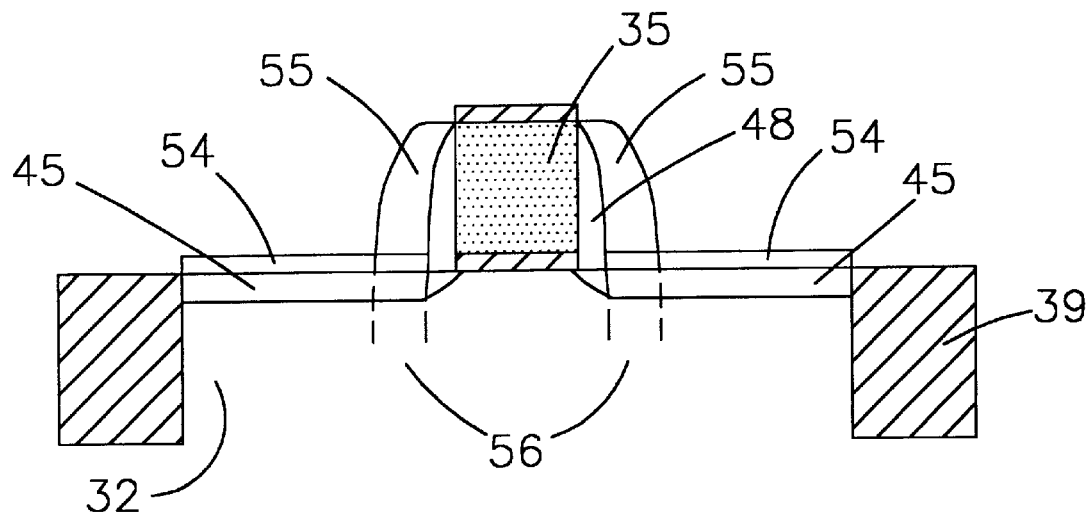
FIG. 5 is a schematic view of the MOSFET in FIG. 4 with second dielectric side spacers, in accordance with the first embodiment of the present invention.

The surface of the substrate 32 is then subjected to a precleaning. A selective silicon (Si) epitaxial growth at a temperature of 750–900° C. is used to grow first semiconductor layers 52 of a thickness of 200–300 Å, as shown in FIG. 4. A low-energy (e.g., 1–3 KeV) dopant implantation 53 is used to transform the first semiconductor layers 52 into raised source/drain extensions 54 with a bottom surface adjacent to the implant junctions 45 and a top surface opposite from the bottom surface, as shown in FIG. 5. In this example an N-type implant is used. A deposit-and-etch-back process using a low temperature chemical vapor deposition at less than 400° C. is used to form second dielectric spacers 55, which are preferably silicon oxide or silicon nitride. The second dielectric spacers 55 each have a width 56 of between 300–800 Å (which is defined as the thickest part of the width of the second dielectric spacers 55). The second dielectric spacers 55 are adjacent to the first dielectric spacers 48 and are separated from the gate 35 by the first dielectric spacers 48. The second dielectric spacers 55 extend from the top of the first dielectric spacers 48 to the top surface of the raised source/drain extensions 54.

Figure 6:
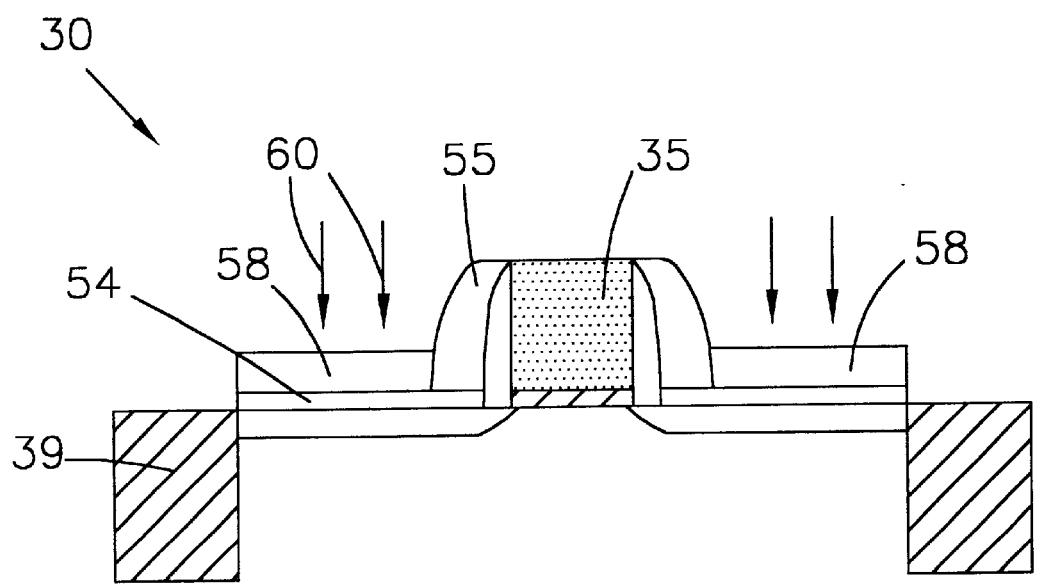
FIG. 6 is a schematic view of the MOSFET in FIG. 5 with a second semiconductor layer, in accordance with the first embodiment of the present invention, (7)

The top surface of the raised source/drain extensions 54 is subjected to a surface preclean. Then a selective Si epitaxial growth at a temperature of 750–900° C. is used to grow second semiconductor layers 58 of a thickness of 200"300 Å on the top surface of the raised source drain extensions 54 and extending from the isolation trenches to the second dielectric spacers 55, as shown in FIG. 6. The anti-reflective coating 41 is stripped. A higher energy (e.g., 10–30 KeV) dopant implantation 60 is used to dope the second semiconductor layers 58, and the gate 35. In this example of a preferred embodiment, an N-type implant is used. A rapid-thermal-anneal (RTA) is used to transform the doped second semiconductor layers 58 into raised source/drain regions.

Conventional MOSFET processing is done to form the MOSFET structure 30 into a completed MOSFET, including the silicidation of the raised source/drain regions, the raised source/drain extensions, the shallow source/drain junctions, and the gate. The resulting MOSFET has partially raised source/drain extensions, providing ultra-shallow source/drain junctions, which reduces the short channel effect. If the implant junctions are part of source/drain extensions the implant junctions may be doped at lower doping levels than in conventional source/drain extensions.

Figure 7:
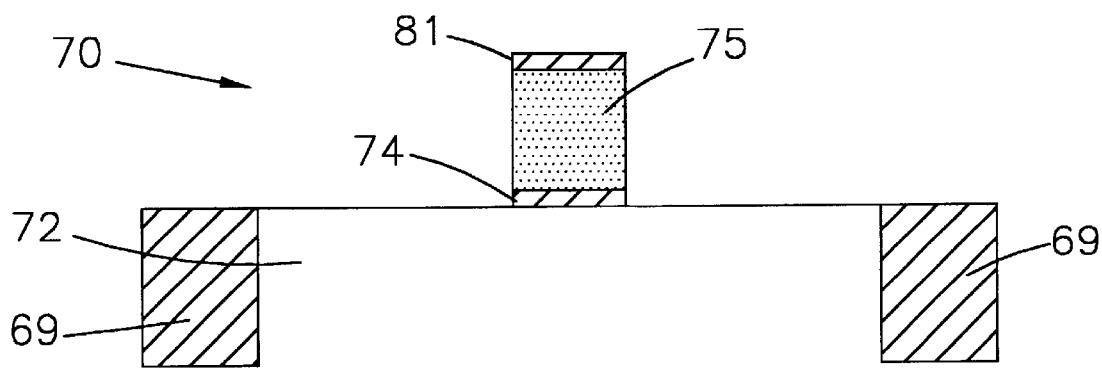
FIG. 7 is a schematic view of a substrate with the first phase of a MOSFET being formed, in accordance with a second embodiment of the present invention.

In another embodiment of the invention, isolation trenches 69 are etched into the surface of the substrate 72 upon which a first phase of a MOSFET 70 is built, as schematically illustrated in FIG. 7. The first phase of the MOSFET 70 has a gate 75 placed on a gate oxide 74 placed on the surface of the substrate 72. An anti-reflective coating (ARC) 81 is placed on the gate 75. In the preferred embodiment, the anti-reflective coating is silicon oxynitride (SiON) with a thickness of 200–300 Å (angstroms).

Figure 8:
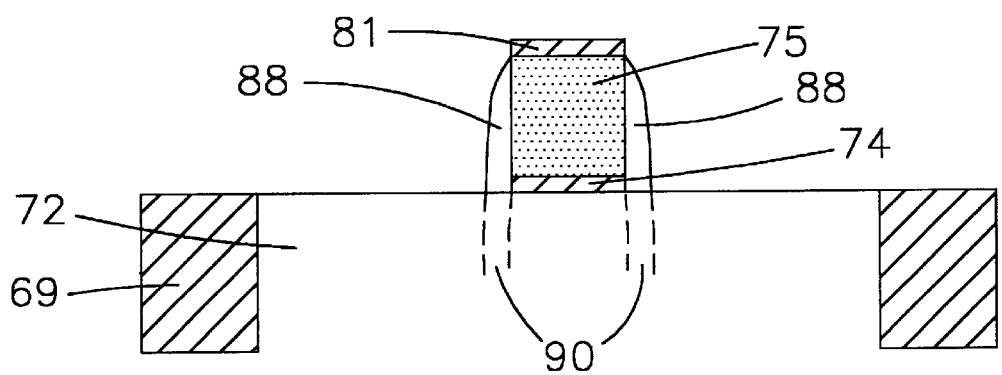
FIG. 8 is a schematic view of the MOSFET in FIG. 7 with first dielectric spacers, in accordance with the second embodiment of the present invention.

In this example of the preferred embodiment, a deposit-and-etch-back process using a low temperature chemical vapor deposition at less than 400° C. is used to form first dielectric spacers 88, which are preferably silicon oxide or silicon nitride, as shown in FIG. 8. The first dielectric spacers 88 each have a width 90 of between 150–200 Å. The first dielectric spacers 88 are adjacent to the sides of the gate 75 and gate oxide 74 and extend from the top of the gate 75 to the surface of the substrate 72.

Figure 9:
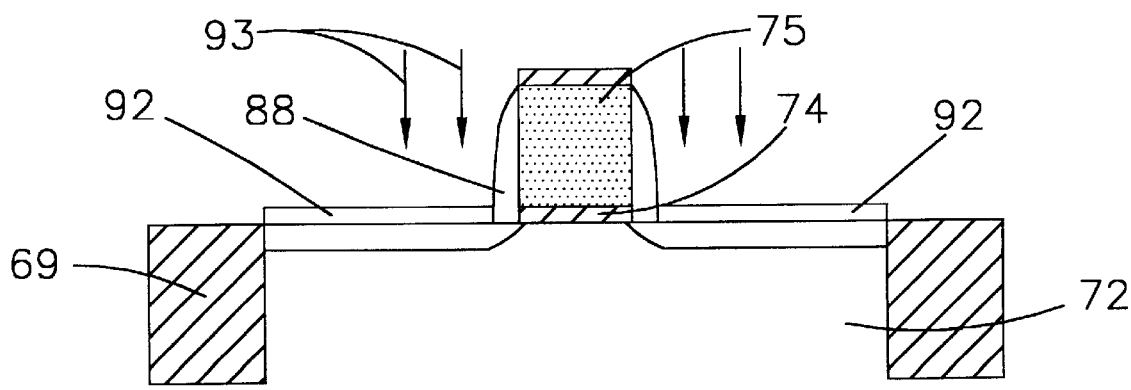
FIG. 9 is a schematic view of the MOSFET in FIG. 8 with a first semiconductor layer, in accordance with the second embodiment of the present invention.
Figure 10:
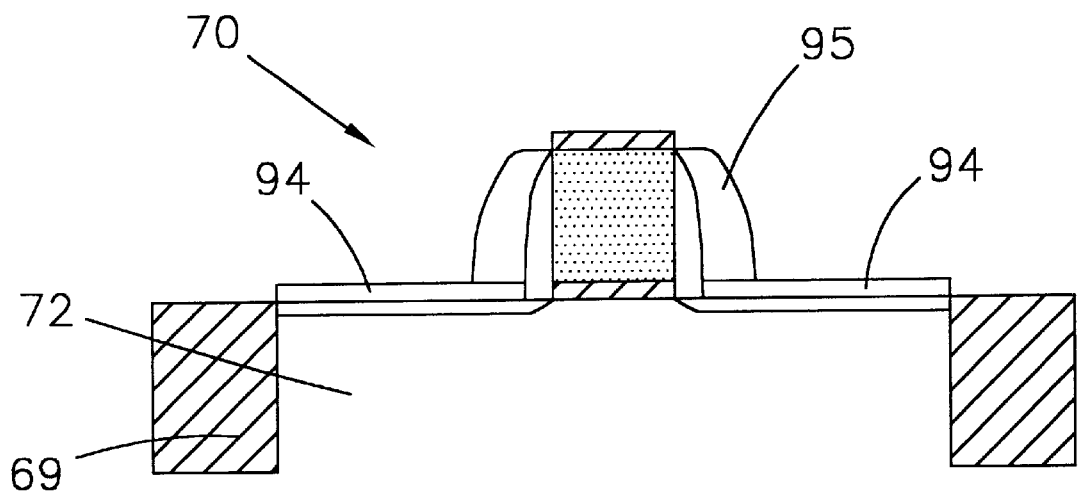
FIG. 10 is a schematic view of the MOSFET in FIG. 9 with second dielectric side spacers, in accordance with the second embodiment of the present invention.

The surface of the substrate 72 is then subjected to a precleaning. A selective silicon (Si) epitaxial growth at a temperature of 750–900° C. is used to grow first semiconductor layers 92 of a thickness of 200–300 Å, as shown in FIG. 9. A low-energy dopant implantation 93 is used to transform the first semiconductor layers 92 into raised source/drain extensions 94 with a bottom surface adjacent to the surface of the substrate 72 and a top surface opposite from the bottom surface, as shown in FIG. 10. In this example an P-type implant, such as boron (B) with an implant energy of 0.5–3 KeV, is used. A deposit-and-etch-back process using a low temperature chemical vapor deposition at less than 400° C. is used to form second dielectric spacers 95, which are preferably silicon oxide or silicon nitride. The second dielectric spacers 95 each have a width 96 of between 300–800 Å. The second dielectric spacers 95 are adjacent to the first dielectric spacers 88 and are separated from the gate 75 by the first dielectric spacers 88. The second dielectric spacers 95 extend from the top of the first dielectric spacers 88 to the top surface of the raised source/drain extensions 94.

Figure 11:
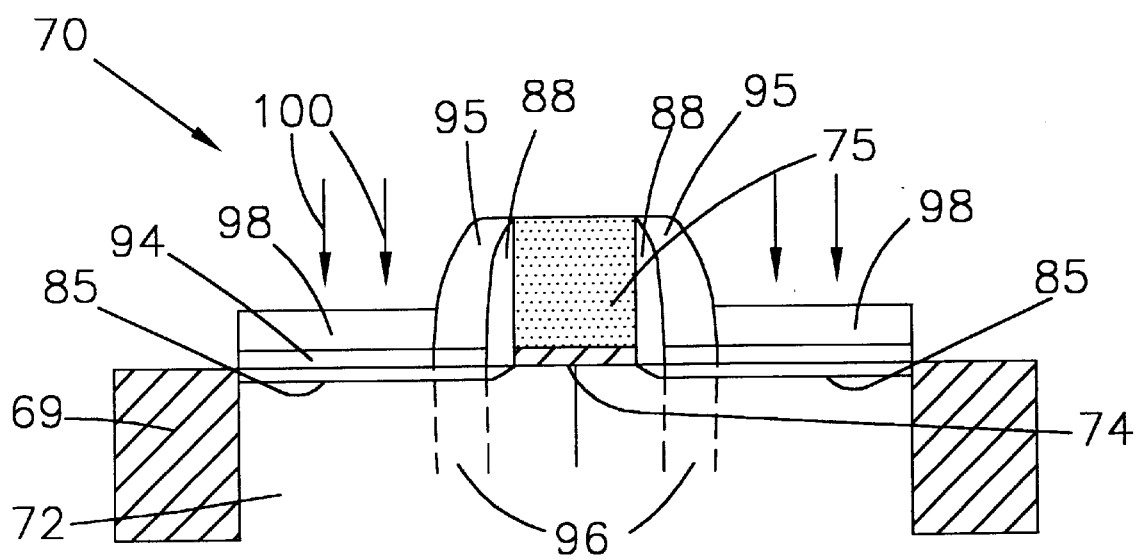
FIG. 11 is a schematic view of the MOSFET in FIG. 10 with a second semiconductor layer, in accordance with the second embodiment of the present invention.

The top surface of the raised source/drain extensions 94 is subjected to a surface preclean. Then a selective Si epitaxial growth at a temperature of 750–900° C. is used to grow second semiconductor layers 98 of a thickness of 200–300 Å on the top surface of the raised source drain extensions 94 and extending from the isolation trenches to the second dielectric spacers 95, as shown in FIG. 11. The anti-reflective coating 81 is stripped. A dopant implantation 100 is used to dope the second semiconductor layers 98, and the gate 75. In this example of a preferred embodiment, a P-type implant, such as boron difluoride ($BF_2$) with an implant energy of 10–30 KeV, is used. A rapid-thermal-anneal (RTA) is used to transform the doped second semiconductor layers 98 into source/drain regions and to complete the tansformation of the doped first semiconductor layers 92 into the raised source/drain extensions 94. The rapid-thermal-annealing also causes some of the P-type implant dopant from the first semiconductor layers 92 to migrate to the surface of the substrate 72 forming on and in the surface of the substrate 72 ultra shallow implant junctions 85, which extend from the isolation trenches 69 under the first dielectric spacers 88 to the gate oxide 74.

Conventional MOSFET processing is done to form the MOSFET structure 70 into a completed MOSFET, including the silicidation of the raised source/drain regions, the raised source/drain extensions, the shallow source/drain junctions, and the gate. The resulting MOSFET has fully raised source/drain extensions with minimal source/drain junction depths in the substrate and optimal overlap distance under the gate 75, which reduces the short channel effect.

Information as herein shown and described in detail is fully capable of attainig the above-described object of the invention, it is understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural and functional equivalents to the elements of the above-described preferred embodiment that are known or later come to be known to those of ordinary still in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. §112, sixth paragraph, unless the element is expressly recited using the phrase "means for."

We claim:

1. A semiconductor device, comprising:

a substrate having an upper surface;

shallow trench isolations formed in the substrate;

a gate oxide formed on the upper surface of the substrate, the gate oxide having a first side adjacent the upper surface of the substrate and a second side opposite the first side;

a gate formed on the gate oxide, the gate having a first side adjacent the second side of the gate oxide and a second side opposite the first side at a top of the gate;

first dielectric spacers formed on the sides of the gate, the first dielectric spacers having a fist side adjacent the gate and a second side opposite the first side, and the first dielectric spacers hang a width in a range of 150 Å to 200 Å;

partially-raised source/drain extensions with a first side adjacent the upper surface of the substrate and a second side opposite the first side, the partially-raised source/drain extensions extending from the first dielectric spacers to the respective shallow trench isolations;

second dielectric spacers with a first side adjacent the first dielectric spacers and a second side opposite the first side, the second dielectric spacers extending from the second side of the partially-raised source/drain extensions to the top of the gate;

second raised source/drain regions, formed by implanted dopants in a second semiconductor layer, with a first side adjacent the second side of the partially-raised source/drain extensions, the second raised source/drain regions extending from the second dielectric spacers to the respective shallow trench isolations; and ultra-shallow source/drain implant junctions beneath the upper surface of the substrate, the ultra-shallow source/drain implant junctions extending from the respective shallow trench isolations to the gate oxide for reducing a short channel effect.

2. A semiconductor device, as recited in claim 1, wherein said ultra-shallow source/drain implant junctions comprise a low-energy dopant implantation.

3. A semiconductor device, as recited in claim 1, wherein each of the second dielectric spacers has a width in a range of 300 Å-800 Å.

4. A semiconductor device, as recited in claim 1, wherein each of the partially-raised source/drain extensions has a thickness in a range of 200 Å-300 Å.

5. A semiconductor device, as recited in claim 1, wherein each of the second raised source/drain regions has a thickness in a range of 200 Å-300 Å.

6. A semiconductor device, as recited in claim 1, wherein at least one structure selected from a group consisting essentially of said gate, said second raised source/drain regions, said partially-raised source/drain extensions, and said ultra-shallow source/drain implant junctions comprises at least one silicide.

7. A semiconductor device, as recited in claim 1, wherein said ultra-shallow source/drain implant junctions comprise an ultra-low-energy dopant implantation.

* * * * *

UNITED STATES PATENT AND TRADEMARK OFFICE
CERTIFICATE OF CORRECTION

PATENT NO.    : 6,445,042 B1
DATED         : September 3, 2002
INVENTOR(S)   : Bin Yu and Judy Xilin An It is certified that error appears in the above-identified patent and that said Letters Patent is hereby corrected as shown below:

Column 2,
Line 52, after "MOSFET" add -- 30 --.

Column 5,
Line 27, delete "hang" and replace with -- having --.

Signed and Sealed this

Fourth Day of February, 2003

JAMES E. ROGAN
*Director of the United States Patent and Trademark Office*